(12) United States Patent
Price et al.

(10) Patent No.: US 9,066,786 B1
(45) Date of Patent: Jun. 30, 2015

(54) LATERALLY APPLIED ORTHOSIS

(76) Inventors: Stephen A. Price, Tampa, FL (US);
Mary P. Price, Tampa, FL (US)

( * ) Notice: Subject to any disclaimer, the term of this patent is extended or adjusted under 35 U.S.C. 154(b) by 171 days.

(21) Appl. No.: 13/075,421

(22) Filed: Mar. 30, 2011

Related U.S. Application Data

(63) Continuation-in-part of application No. 12/559,111, filed on Sep. 14, 2009.

(51) Int. Cl.
| | | |
|---|---|---|
| *A61F 5/00* | (2006.01) | |
| *A63B 21/02* | (2006.01) | |
| *A61F 5/01* | (2006.01) | |
| *A63B 21/00* | (2006.01) | |
| *A63B 23/035* | (2006.01) | |

(52) U.S. Cl.
CPC ............. *A61F 5/0102* (2013.01); *A61F 5/0106* (2013.01); *A61F 5/0104* (2013.01); *A61F 5/0118* (2013.01); *A63B 21/02* (2013.01); *A63B 21/1403* (2013.01); *A63B 21/1449* (2013.01); *A63B 23/035* (2013.01)

(58) Field of Classification Search
CPC ........... A61F 5/00; A61F 5/01; A61F 5/0102;
A61F 5/0104; A61F 5/0106; A61F 5/0118;
A63B 21/00; A63B 21/002; A63B 21/0023;
A63B 21/02; A63B 21/055; A63B 21/0552;
A63B 21/0555; A63B 21/14; A63B 21/1403;
A63B 21/1423; A63B 21/1434; A63B
21/1446; A63B 21/1449; A63B 21/1484;
A63B 23/00; A63B 23/035; A63B 23/03508;
A63B 23/04; A63B 23/0494; A63B 23/12;
A63B 23/1281

USPC .......... 602/5, 6, 20–27, 60–65; 128/878–882;
482/91, 105, 121, 122, 124, 148
See application file for complete search history.

(56) References Cited

U.S. PATENT DOCUMENTS

| | | | |
|---|---|---|---|
| 5,891,068 A | 4/1999 | Kenney | |
| 5,921,945 A * | 7/1999 | Gray | ................................. 602/5 |
| 6,001,074 A | 12/1999 | Kenney | |
| 6,206,846 B1 | 3/2001 | Kenney | |
| 6,261,253 B1 | 7/2001 | Katzin | |
| 6,656,097 B2 * | 12/2003 | Karecki | ........................ 482/148 |
| 6,692,453 B2 * | 2/2004 | Wolfe | ............................. 602/21 |
| 2005/0038367 A1 * | 2/2005 | McCormick et al. | ........... 602/26 |
| 2007/0055191 A1 * | 3/2007 | Farrell et al. | .................... 602/21 |
| 2009/0320299 A1 * | 12/2009 | Kuhn et al. | ..................... 30/169 |

\* cited by examiner

*Primary Examiner* — Alireza Nia
*Assistant Examiner* — Keri J Nelson
(74) *Attorney, Agent, or Firm* — Dale J. Ream

(57) ABSTRACT

A laterally applied orthosis having a dynamic flexible stiffener that is configured to extend across a joint and impede joint movement caused by muscle contractions by resisting flexing but allowing some movement in the joint. The stiffener is elastic so that it rebounds to its original form after flexing due to movement of the joint. The stiffener is disposed within a brace having a plurality of adjustable straps extending from the brace. The straps can be fastened to one another or the brace itself to form a substantially tubular structure for securing the brace to a limb. At least one of the plurality of straps is semi-rigid and malleable.

1 Claim, 5 Drawing Sheets

LATERALLY APPLIED ORTHOSIS

CROSS REFERENCE TO RELATED APPLICATION

This application claims priority to, and is a continuation-in-part of, currently pending U.S. patent application Ser. No. 12/559,111, entitled "ORTHOSIS," filed on Sep. 14, 2009, the contents of which are hereby incorporated by reference.

BACKGROUND OF THE INVENTION

1. Field of the Invention

This invention relates to an orthosis. More specifically, it relates to a laterally applied orthosis having a flexible stiffener.

2. Description of the Related Art

Patients that have neurological disorders such as cerebral palsy and multiple sclerosis, muscular disorders, stroke victims, or persons with spinal cord injuries often uncontrollably contract their joints in flexion, which can cause the patients to lose range of motion in their joints. Common joints that are affected by patients having these conditions include wrist joints and finger joints, foot, toe, and ankle joints, hip joints, elbow joints, and knee joints. In an attempt to treat or otherwise alleviate the potential loss of range of motion due to conditions like those set forth above, doctors and physical therapists often secure an orthosis or splint across the affected joint to prevent uncontrollable flexion of the joint by stretching the joint to a desired position. The orthosis may be moved to a series of desired positions to stretch the joint and hopefully prevent a loss of range of motion.

Many different types of orthoses have been developed that stretch joints to a desired position thereby preventing patients wearing the orthoses from uncontrollably contracting their joints in flexion. For example, U.S. Pat. No. 6,261,253 to Katzin discloses a hand orthosis that limits finger and wrist flexion with a steel stiffener that provides a static resistance to the user. The stiffener is plastically deformed into the desired position to conform to the shape of the joint and surrounding limbs. However, the stiffener is made of material such that it will resist forces to which it is normally subjected when worn by a patient. That is, during contracture, the patient is unable to move the stiffener during use such that the stiffener provides a static resistance to the joint. While this property is useful in many circumstances, the needs of certain patients require a different type of stiffener.

The assignee of the present application has also developed knee and elbow orthoses for treatment of undesirable flexural contractions of those joints. These knee and elbow orthoses utilize goniometers which are adjustable to allow a certain degree of joint movement. For example, if zero degrees represents the angle of a patient's arm or leg when it is straight, then the goniometer can be adjusted so that the patient can only move his or her arm or leg a predetermined number of degrees freely within the range of movement allowed by the goniometer. For some patients it is undesirable to use an orthosis that allows this type of movement, even if it is only within a certain range.

Thus, while orthoses have been used to treat or alleviate the symptoms of uncontrollable joint flexion, there is a need for the type of orthosis that is disclosed in the present application.

SUMMARY OF THE INVENTION

The novel laterally applied orthosis has a dynamic, flexible stiffener that is configured to extend across a joint and impede joint movement caused by muscle contractions by resisting flexing but allowing some movement in the joint. The stiffener is elastic so that it rebounds to its original form after flexing due to movement of the joint.

The orthosis may be used to impede the movement of any joint. Preferably, however, the orthosis impedes movement of the wrist and finger joints, the elbow joint, the knee joint, the hip joint, or the ankle and toe joints by having the flexible stiffener extend across the respective joint. Because the stiffener is elastic, it allows joint movement but constantly provides resistance to the movement until the joint returns to its repose position.

For certain patients, the stiffener is better than conventional orthoses at preventing loss of range of motion due to its dynamic properties. It is believed that the ability of the stiffener to provide a patient's joint with a range of motion, while resisting that joint motion, assists in preventing degeneration of the joint and the muscles connected to it. This feature is not present in the conventional orthoses described above, which cannot be moved by the patient.

Moreover, the orthosis enables a user to apply it laterally to the joint, regardless of joint contraction due to muscle flexion. Specifically, the dynamic, flexible stiffener within the orthosis is bent to correspond with the contraction angle of the joint. The orthosis is then positioned on the joint by laterally sliding the flexed stiffener adjacent to the contracted joint. The stiffener is released and applies a constant force to the contracted joint. This lateral positioning of the orthosis on the contracted joint cannot be accomplished with the conventional orthoses described above without undue difficulty.

In an embodiment, the orthosis extends across a patient's elbow joint and includes a dynamic, flexible, elastic stiffener for impeding movement caused by muscle contraction. The stiffener includes a first configuration extending across the elbow joint of the patient when the patient's muscle is in repose and a second configuration extending across the elbow joint of the patient when the patient's muscle is under contraction. The stiffener allows some joint movement but resists flexion of the elbow joint to impede joint movement. The stiffener rebounds from the second configuration to the first configuration after the contraction has terminated.

The stiffener is disposed within a brace. The brace is configured to receive an arm and includes a medial side and a lateral side. When positioned on the patient, the brace extends from an upper arm to a forearm. The stiffener is disposed within the brace such that the stiffener extends from the medial side of the upper arm to the medial side of the forearm for impeding movement of the elbow joint.

A plurality of straps extends from the brace and is adapted to be fastened to one another or to the brace itself to form a substantially tubular structure for securing the brace to the arm. At least one of the plurality of straps is semi-rigid and malleable. The semi-rigid, malleable strap enables the brace to be positioned on the user from the side, thereby limiting the amount of movement required by the user to position the brace. Moreover, the semi-rigid, malleable strap may be substantially C-shaped, further limiting the amount of movement required by the user to position the brace.

Another embodiment of the novel orthosis impedes movement of a knee joint caused by muscle contraction. Like the elbow orthosis disclosed above, the knee orthosis includes a stiffener, a brace, and a plurality of adjustable straps for securing the brace to a patient's leg. The brace is positioned on the posterior side of the patient's leg and is configured to retain the flexible dynamic stiffener. The stiffener extends from the posterior side of the upper leg to the posterior side of the lower leg for impeding movement of the knee joint.

The flexible dynamic stiffener for any of the embodiments described above may include a heat treated and tempered spring steel. In one aspect, the spring steel is Unified Numbering System G10950 steel. Preferably, the stiffener includes steel having a yield tensile strength of between approximately 100 to 320 kilopounds per square inch, more preferably between approximately 150 to 275 kilopounds per square inch, even more preferably between approximately 200 to 250 kilopounds per square inch, and most preferably approximately 240 kilopounds per square inch. In one aspect, the stiffener comprises steel having a modulus of elasticity of between approximately 150 to 300 GPa, more preferably between approximately 175 to 250 GPa, and most preferably between approximately 190 to 210 GPa. Preferably, the stiffener includes steel having a hardness on the Rockwell C scale of between approximately 45 to 60, more preferably between approximately 45 to 55, and most preferably between approximately 48 to 51.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The novel laterally applied orthosis includes a flexible dynamic stiffener that is configured to extend across a joint and is elastic such that it rebounds to its original form after flexing due to joint movement caused by muscle contraction. While the orthosis could be designed to be used in conjunction with any articulating joint, two types of orthoses are disclosed herein for illustration. Thus, while elbow and knee orthoses are disclosed herein, any type of orthosis having a flexible dynamic stiffener as disclosed herein, including a hand/wrist, foot/ankle/toes, hip/knee, and hip/thigh orthosis, is within the scope of this invention.

Figure 1:
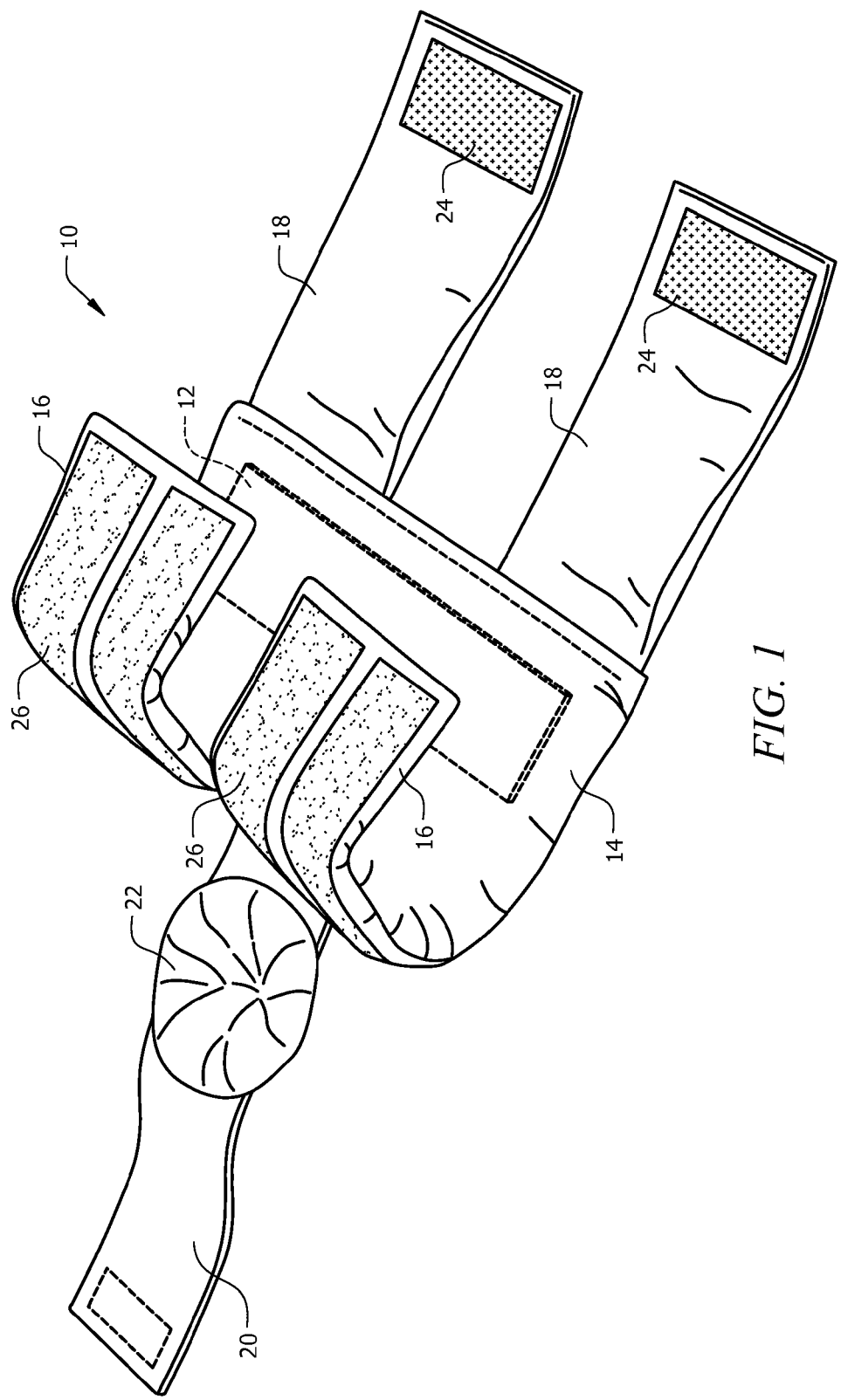
FIG. 1 is an upper perspective view of the orthosis in an open configuration.
Figure 2:
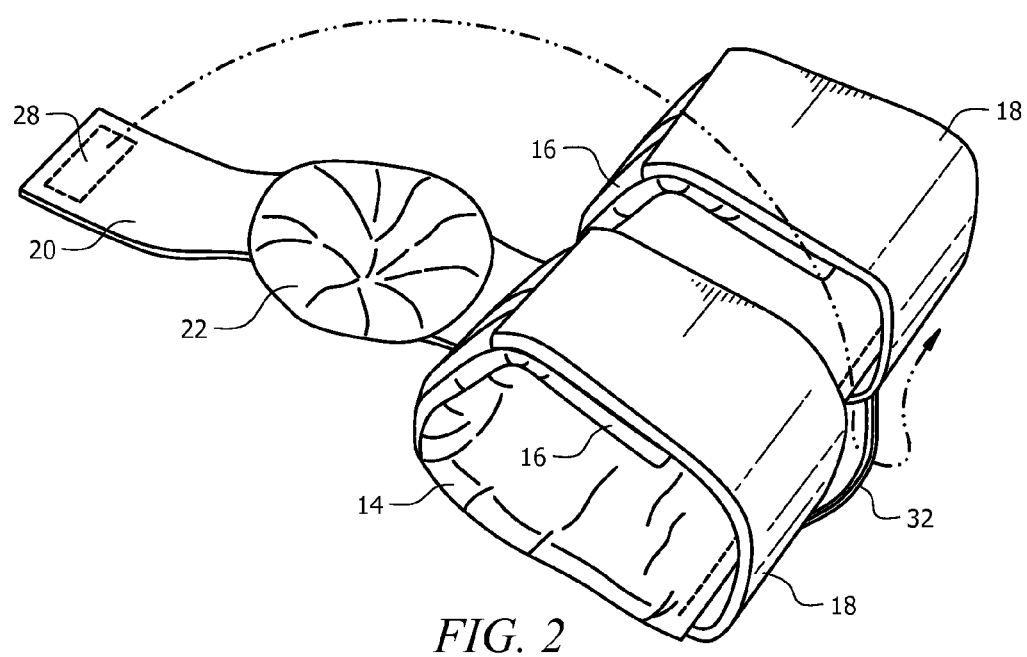
FIG. 2 is an upper perspective view of the orthsis in a partially closed configuration.
Figure 3:
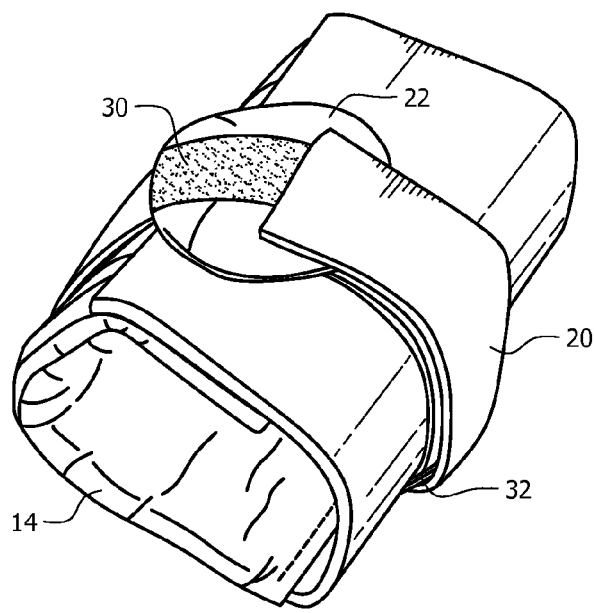
FIG. 3 is an upper perspective view of the orthsis in a closed configuration.

As depicted in FIGS. 1-3, the novel orthosis is generally denoted as 10 and includes flexible stiffener 12 disposed within brace 14. Flexible stiffener 12 is of the same type described in detail for a knee and elbow orthosis in currently pending U.S. patent application Ser. No. 12/559,111, entitled "ORTHOSIS," filed on Sep. 14, 2009, and is hereby incorporated by reference.

Straps 18 extend from brace 14 and are adapted to be fastened to semi-rigid and malleable straps 16 or to brace 14 to form a substantially tubular structure for securing brace 14 to a knee or elbow. Semi-rigid, malleable straps 16 are substantially C-shaped and facilitate the placement of brace 14 on a user. Specifically, semi-rigid, malleable, C-shaped straps 16 enable orthosis 10 to be positioned on a user from the side without having to move or adjust their arm or leg. The outer surface of semi-rigid and malleable straps 16 include loops 26, and the distal ends of straps 18 include hooks 24. Hooks 24 and loops 26 secure straps 18 and semi-rigid and malleable straps 16 together to form said substantially tubular structure.

Knee strap 20 extends from brace 14 and includes knee pad 22. Knee strap 20 is wrapped around brace 14 to further form said substantially tubular structure and protects a knee or elbow of a user. The distal end of knee strap 20 includes hooks 28, and the outer surface of knee strap 20 includes loops 30. Knee strap 20 is folded over brace 14 and inserted through loop 32. Hooks 28 and loops 30 are then secured together.

Figure 4:
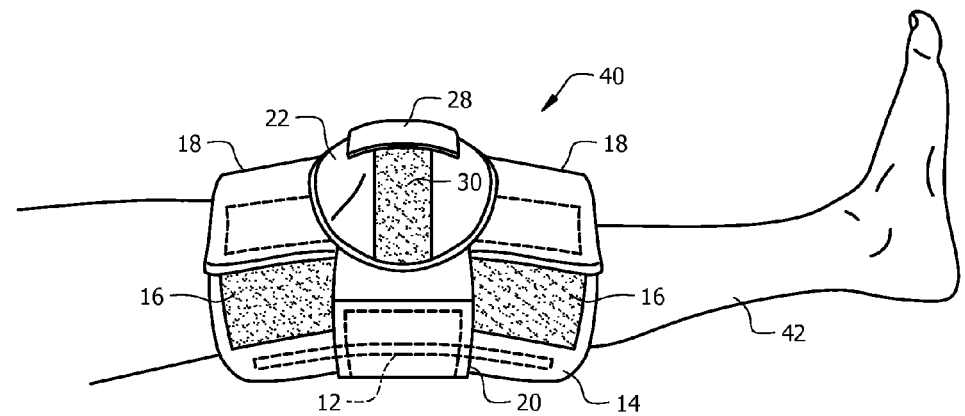
FIG. 4 is an upper perspective view of the orthosis positioned on a patient's extended leg.
Figure 5:
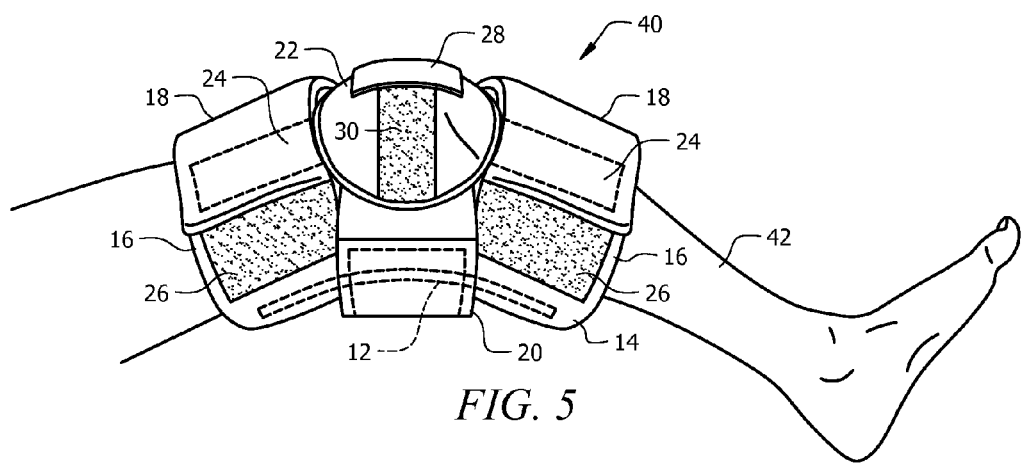
FIG. 5 is an upper perspective view of the orthosis positioned on a patient's partially contracted leg.
Figure 6:
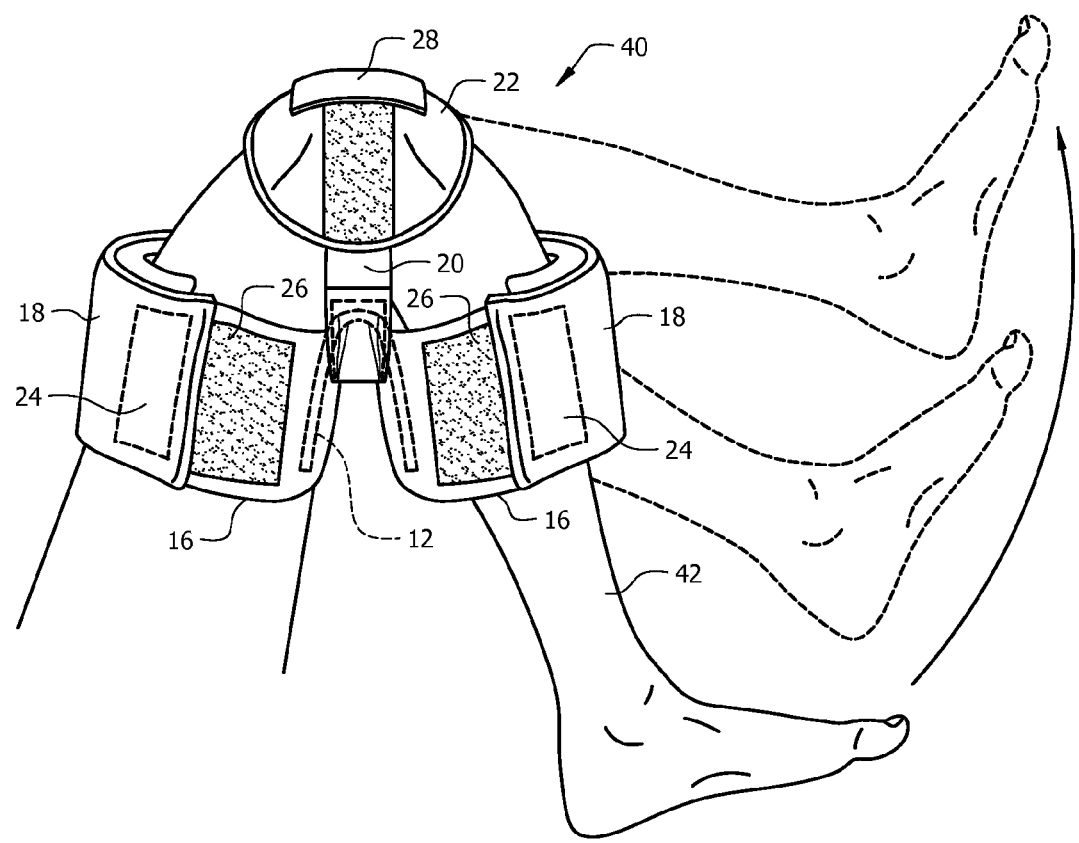
FIG. 6 is an upper perspective view of the orthosis positioned on a patient's fully contracted leg.

A knee orthosis according to an embodiment of the present invention is depicted generally as 40 in FIGS. 4-6. Knee orthosis 40 is substantially similar to an elbow orthosis except that knee orthosis 40 is slightly larger so that it can receive leg 42 and impede movement of a knee. Knee orthosis 40 includes flexible stiffener 12 (not shown) disposed within brace 14. Straps 18 extend from brace 14 and are adapted to be fastened to semi-rigid and malleable straps 16 or to brace 14 to form a substantially tubular structure for receiving leg 42. Semi-rigid, malleable straps 16 are substantially C-shaped and facilitate the placement of brace 14 on leg 42. The outer surface of semi-rigid and malleable straps 16 include loops 26, and the distal ends of straps 18 include hooks 24. Hooks 24 and loops 26 secure straps 18 and semi-rigid and malleable straps 16 together to form said substantially tubular structure. Knee strap 20 extends from brace 14 and includes knee pad 22. Knee strap 20 is wrapped around brace 14 to further form said substantially tubular structure and protects the knee of leg 42. The distal end of knee strap 20 includes hooks 28, and the outer surface of knee strap 20 includes loops 30. Hooks 28 and loops 30 are secured together.

As depicted in FIG. 4, flexible stiffener 12 is in a repose position when leg 42 is not contracted. As depicted in FIG. 5, however, flexible stiffener 12 is partially flexed as leg 42 is partially contracted. Likewise, as depicted in FIG. 6, flexible stiffener 12 is fully flexed when leg 42 is fully contracted. In both FIGS. 5 and 6, flexible stiffener 12 provides a constant resistance to impede joint movement caused by muscle contractions. Once the muscle is no longer contracted, the orthosis returns to the repose position as depicted in FIG. 4.

As depicted in FIG. 6, orthosis 40 enables a user to apply it laterally to the joint, regardless of joint contraction due to flexion. Specifically, flexible stiffener 12 within orthosis 40 is bent, relative to its position of repose, to correspond with the contraction angle of the joint. Orthosis 40 is positioned adjacent to the joint by laterally sliding the flexed flexible stiffener 12 under the contracted joint. Flexible stiffener 12 is then released, so that its inherent bias attempts to return it to its position of repose, thereby applying a constant force to the contracted joint and urging it into a straightened position. As the stiffener rebounds to its repose position, it resists flexion of the muscles causing the contraction, tiring the muscles and eventually straightening the joint. As a result, the joint will go from the configuration in FIG. 6 to FIG. 5 and eventually to FIG. 4. Stiffener 12 has returned to its position of repose in said FIG. 4.

Figure 7:
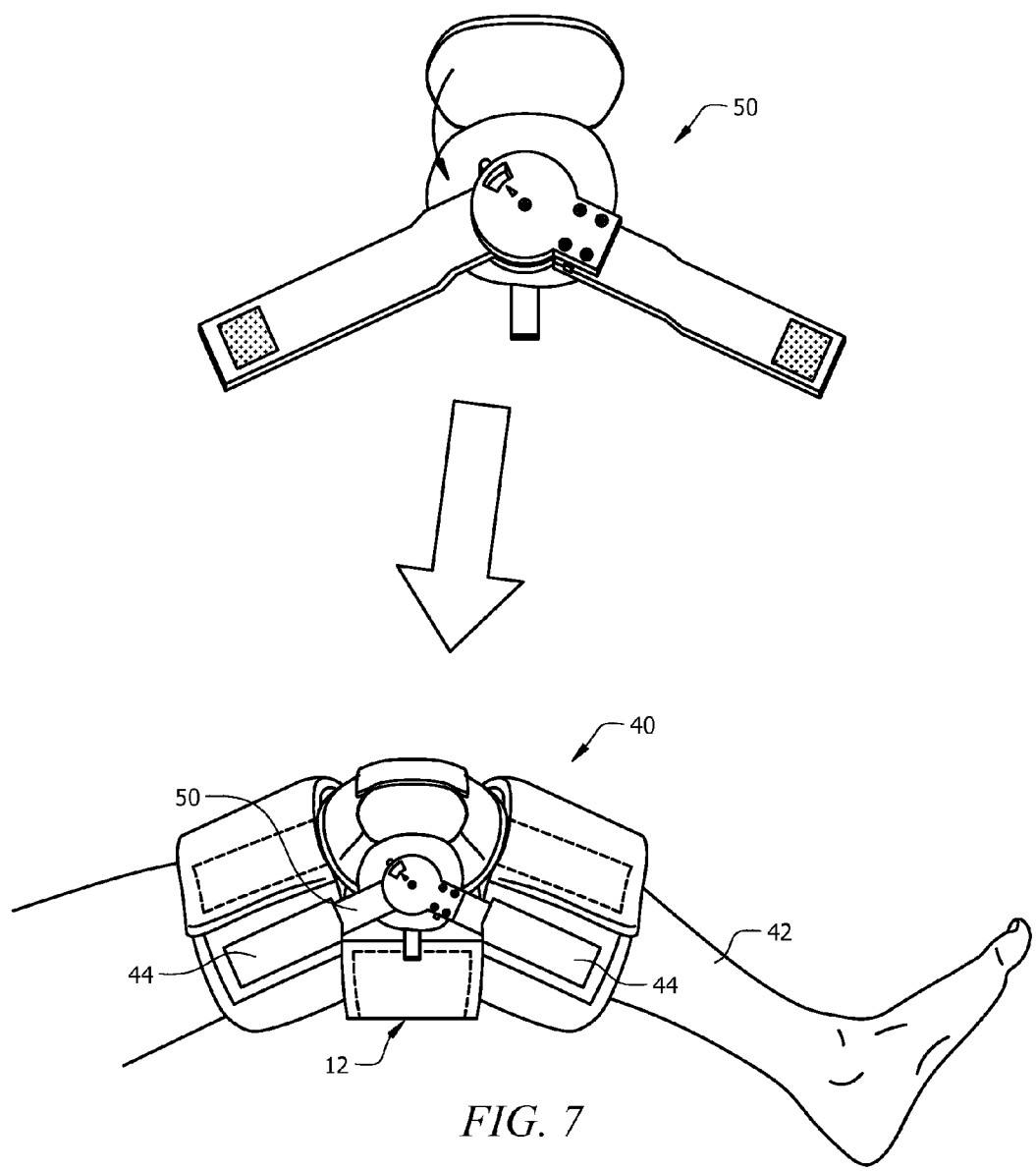
FIG. 7 is an upper perspective view of the orthosis including a goniometer.

In an embodiment, as depicted in FIG. 7, goniometer 50 may be attached to the lateral side of knee orthosis 40. Knee orthosis 40 may include pockets 44 disposed on the lateral side of brace 14 for receiving a corresponding end of goniometer 50. Goniometer 50 is adjustable to allow/prevent a certain degree of joint movement. Goniometer 50 may include any goniometer known in the art. The goniometer works in conjunction with flexible stiffener 12 to prevent a user from completely contracting leg 42. For example, if zero degrees represents the angle of a patient's arm or leg when it is straight, then the goniometer can be adjusted so that the patient can only move his or her arm or leg a predetermined number of degrees freely within the range of movement allowed by the goniometer. Within the range of movement allowed, however, flexible stiffener 12 provides constant resistance to joint movement.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A method of laterally applying an orthosis having a dynamic, flexible, elastic stiffener to an uncontrollably contracted joint, said uncontrollably contracted joint that resists said straightening, comprising the steps of:

providing an elongate orthosis that is moldable into a C-shaped in transverse section so that said orthosis has a longitudinally-extending opening along its extent that is adapted to receive a bent limb having said uncontrollably contracted joint without requiring said bent limb to be unbent to any degree;

forming said stiffener to have a rectangular structure, a flat position of repose, a uniform thickness, and providing said stiffener with an inherent bias that returns said stiffener to said flat position of repose when said stiffener is bent to any preselected angle;

bending said bent stiffener adjacent to said uncontrollably contracted joint by laterally sliding the stiffener under the uncontrollably contracted joint so that the user need not move or adjust the position of the limb having said uncontrollably contracted joint;

said stiffener formed of heat-treated and tempered spring steel;

said heat-treated and tempered spring steel having a yield tensile strength of about 100 to 320 kilopounds per square inch;

said heat-treated and tempered spring steel having a modules of elasticity of about 150 to 300 GPA;

said heat-treated and tempered spring steel having a thickness of about 0.008 to 0.97 inches;

said heat-treated and tempered spring steel having a hardness of about 45 to 60 on the Rockwell C scale; and said inherent bias being sufficient to overcome said uncontrolled contraction so that said limb is urged to straighten when said uncontrolled contraction ends.

\* \* \* \* \*